United States Patent [19]

Cammann

[11] Patent Number: 5,445,726
[45] Date of Patent: Aug. 29, 1995

[54] PROCESS AND DEVICE FOR PROLONGING THE USAGE TIME AND REDUCING THE TEMPERATURE DEPENDENCE OF ION-SELECTIVE POLYMER MEMBRANE ELECTRODES

[75] Inventor: Karl Cammann, Münster, Germany

[73] Assignee: Daimler-Benz Aerospace AG, Munich, Germany

[21] Appl. No.: 157,192

[22] Filed: Jan. 27, 1994

[30] Foreign Application Priority Data

Apr. 10, 1992 [DE] Germany .................. 42 12 149.3

[51] Int. Cl.[6] ............................................. G01N 27/26
[52] U.S. Cl. ........................... 204/153.22; 204/153.12; 204/153.14; 204/153.1; 204/418; 204/403; 204/409; 204/435; 204/408; 204/402
[58] Field of Search ............... 204/418, 409, 403, 435, 204/153.14, 153.22, 153.12, 408, 402, 153.1

[56] References Cited

U.S. PATENT DOCUMENTS

| | | | |
|---|---|---|---|
| 4,409,088 | 10/1983 | Kanno et al. | 204/418 |
| 5,078,856 | 1/1992 | Yamaguchi | 204/418 |

FOREIGN PATENT DOCUMENTS 0068505  1/1983  European Pat. Off. .

*Primary Examiner*—John Niebling
*Assistant Examiner*—Bruce F. Bell
*Attorney, Agent, or Firm*—McGlew and Tuttle

[57] ABSTRACT

Device for prolonging the effective usage time (service life), arrangement and process for minimizing temperature effects in any ion-selective polymer membrane electrode measuring chain (ISPE measuring chain), wherein one solution or both solutions directly adjoining the polymer membrane (outer measuring solution and inner potential drain solution) are saturated or supersaturated with the compounds which normally tend to bleed out; and wherein the isotherm intersection of an ion-selective measuring chain with redox drain elements is optimally located in the middle of the measuring range such that this middle is located at ca. 0 mV.

The device may be used for monitoring of groundwater with opposite changes in the concentrations of nitrate and ammonium, evaluated in a special device, with electronic data processing and intermediate data storage (in RAM pack) at the site of the measurement and data polling as needed to a central unit by telemetry.

21 Claims, 3 Drawing Sheets

Fig. 1a

Conventional Measuring Chain

(PRIOR ART)

Fig. 1b

Measuring Chain according to the present invention

1: T = 323 K (ca. 64 mV/decade of activity)
2: T = 298 K (ca. 59 mV/decade of activity)
3: T = 273 K (ca. 54 mV/decade of activity)

PROCESS AND DEVICE FOR PROLONGING THE USAGE TIME AND REDUCING THE TEMPERATURE DEPENDENCE OF ION-SELECTIVE POLYMER MEMBRANE ELECTRODES

FIELD OF THE INVENTION

This application is a 371 of PCT/EP92/01838 filed on Aug. 12, 1992.

The present invention pertains to an electrode measuring chain consisting of an ion-selective membrane electrode based on plastics containing plasticizing agent(s) and so-called electroactive phase(s) (polymer membrane measuring electrode) and of a constant-potential reference electrode. A device and a process for prolonging the usage time of such a measuring chain are disclosed, and an advantageous arrangement with such electrodes for the on-line monitoring of groundwater is described. The groundwater monitoring system disclosed utilizes as the hazard indicator the opposite changes in the nitrate and ammonium ion concentrations before and after flow through a landfill or an abandoned polluted area. Consequently, especially nitrate- and ammonium-selective polymer membrane measuring electrodes will be described as important examples of the prolongation of service life.

BACKGROUND OF THE INVENTION

Ion-selective potentiometry has proved to be highly successful as an important method for determining free ion concentrations since various, more or less selective electrodes for certain cations and anions had become commercially available in the 1960s and since the publication of the first monographs K. Cammann, "Das Arbeiten mit ionenselektiven Elektroden" 1. Auflage, Springer Verlag, Berlin, 1973 on this analytical method, which is called the renaissance of the pH-measuring technique. From the viewpoint of the measuring technique, ion-selective potentiometry extensively corresponds to the conventional pH-measuring technique based on the extremely selective pH-glass membrane electrodes. Only an ordinary constant-potential reference electrode (e.g., one based on calomel or Ag-/AgCl), as well as a correspondingly high-ohmic millivoltmeter (pH meter) with an accuracy of ±0.1 mV are needed for the accurate determination of certain ion concentrations, besides the corresponding measuring electrode that is selective for the ion to be determined. Ion concentrations between the saturation limit and a few ppb can be reliably determined with a measuring arrangement of such a simple design. The quality of the analytical results (i.e., the accuracy of the analysis) is usually determined by the ion-selective measuring electrode. It operates selectively and reversibly as a true chemosensor, i.e., it is able to indicate changes in concentrations in both directions, unlike test bars or test tubes. This is an absolutely necessary requirement for continuous on-line measurements.

The relationship between the measuring chain voltage and the concentration of an ion to be determined is described, to a sufficient accuracy, by an expanded Nernst equation:

$$U = U^o + R\,T/z_M F \ln (c_M + K_{M\text{-}I} c_I^{z_M/z_I})$$

in which U = measuring chain voltage, $U_o$ = measuring chain voltage at ln = 1,
R = Faraday's constant,
T = temperature,
$z_M$ = value and charge of the measured ion,
$z_I$ = value and charge of the interfering ion,
$c_M$ = concentration of the measured ion,
$c_I$ = concentration of the interfering ion, and
$K_{M\text{-}I}$ = selectivity coefficient between the measured ion and the interfering ion.

It is assumed in this analysis function that the ionic strength does not change between calibration and measurement. A slight preparation of the sample solutions by dilution with an ionic strength-adjusting solution, which may also contain masking chemicals for particularly interfering ions, may be necessary under certain circumstances. Flow injection analysis (FIA) is an especially elegant type of sample preparation, which can be automated. Only a few microliters of sample are injected here into a carrier flow of a suitable electrolyte, which flows past the measuring chain (flow-measuring cell) at a rate in the range of mL/minute, and the peak height that develops is used for quantification. Depending on the effective flow rate of the basic (carrier) electrolyte and the dead volume of the potentiometric measuring chain, it is possible to inject 60 samples per minute, which is tantamount to a quasi-continuous measurement (time constant ca. 1 minute). The advantage of the combination of the prior-art flow injection technique with ion-selective potentiometry was soon recognized J. Ruzicka, E. H. Hansen: "Flow Injection Analysis" Wiley, New York, 1981. The carrier liquid flow (carrier solution) can thus be optimized for the measuring electrode in question. By selecting a suitable composition of this basic electrolyte, it is also possible to build a measuring chain without conversion with this combination, which also offers advantages in terms of design engineering, besides increased accuracy (no fluctuating diffusion potential at the reference electrode-electrolyte/-measuring solution phase boundary), because it becomes unnecessary to provide an additional reference electrode electrolyte solution for prolonged on-line operation, or such solution is provided by the FIA carrier solution.

The usage time that can be achieved under real conditions is very important when ion-selective potentiometry is used for continuous measurement analogously to the pH flow fixtures or within the framework of an FIA arrangement. Unlike other membrane electrodes with renewing or renewable surfaces, the class of the so-called liquid membrane electrodes has only a limited service life under these measurement conditions in its most significant design with a polymer-solidified, liquid-like membrane (mostly on the basis of PVC, siloxane, polyacrylamide, etc.). The service life, i.e., the guarantee of the central electroanalytical criteria, such as selectivity, detection limit, Nernst behavior, stability, and speed of indication, of such polymer membrane electrodes is generally restricted by two effects:

a) The bleeding of selectivity-generating membrane components (plasticizing agent and electroactive compound) and b) Impairment of the ratio of the standard exchange current density of measured ions to interfering ions because of the slow increase in the concentration of interfering ions in the membrane phase.

SUMMARY AND OBJECTS OF THE INVENTION

It is an object of the present invention to provide a device and a process with which the effects described in a) and b) are prevented or drastically reduced in order to make possible the use in long-life on-line monitors.

This task is accomplished, on the one hand, by design measures, by preventing the effect according to a) by having only solutions which are saturated or supersaturated with compounds which tend to bleed at the ion-selective polymer membrane directly adjacent to the ion-selective polymer membrane. In other words, the present invention pertains to a device and a process which make it possible to condition the so-called outer and inner solutions of an ion-selective polymer membrane electrode such that the driving force for the bleeding (=distribution between the usually lipophilic polymer membrane and the immediately adjacent, usually aqueous solutions), namely, the chemical potential gradient at the interphases in question, becomes nearly zero.

The second factor (effect b), which influences the service life or usage time of an ion-selective polymer membrane electrode, is optimized according to the present invention by increasing the standard current density for the measured ion in question in relation to all potentially interfering ions by adding a salt of the measured ion (measured ion with a counterion), which is poorly soluble in aqueous solutions, as an additional component to the ion-selective polymer membrane.

As an alternative or in addition to this, the object can also be attained by a continuous conditioning of both membrane surfaces with the measured ion, except during the actual measuring process. The increase that can be observed during the use of such membrane electrodes in the standard exchange current density, especially for more lipophilic interfering ions, which increasingly reduce the selectivity, can be reduced according to the present invention by depleting them by a suitable distribution equilibrium prior to contact with the measuring electrode surface. All the measures according to the present invention were tested with respect to an ammonium-selective and a nitrate-selective polymer membrane electrode as examples, and they showed, in combination, not only a drastic improvement in the usage time by a factor of $>4$ (i.e., $>6$ months in the case of direct contact with a large sample volume in the m$^3$/day range), but also an improvement in the stability of the Nernst factor (slope of the calibration curve (U versus log cM)) and in the detection limit. It is only as a result of these improvements according to the present invention that the various and obviously different polymer membrane compositions can be used for measuring electrodes in long-life on-line monitors (e.g., those positioned in the aquifer for monitoring of groundwater) for the great variety of measured ions. The devices and processes according to the present invention for prolonging the usage time are combined with a new evaluation process for monitoring landfills and abandoned polluted areas by means of an on-line ammonium and nitrate monitor. Even though a groundwater monitoring device equipped with these new electrodes is also described in this disclosure, the improvements according to the present invention are generally valid and apply to all ion-selective measuring chains which have a measuring electrode with polymer membranes.

The state of the art related to the ammonium and nitrate ions, which are important for groundwater monitoring tasks, shows a number of publications and patents on the subject of the ammonium or nitrate-selective polymer membrane electrode, which were all optimized in terms of selectivity and the detection limit for purely synthetic solutions. There has been no prior publication concerning the combination of the different, service life-prolonging measures, or concerning the ammonium and nitrate concentration values in the groundwater in the area surrounding leaking landfills or abandoned polluted areas, which concentration values change in opposite directions. The basic idea of the application of devices according to the present invention in a certain measuring method is the fact that anaerobic conditions occur in all older landfills and/or abandoned polluted areas in the central area, which can communicate with the groundwater in the case of leaks. The microorganisms that are usually present there are able to reduce nitrate ions into ammonium ions. As a result, there is a drastic change in the $NO_3^-$:$NH_4^+$ ratio when the values measured in the upstream are compared with the values measured in the downstream (groundwater flow through a leaking landfill or abandoned polluted area).

The state of the art as well as the general state of knowledge in this area has shown no suggestions so far for solving the problem of the limited usage time of ion-selective electrodes based on a polymer membrane, especially in the case of the flow measurement of large volumes of measured solutions. In addition, there are no publications concerning the combination of long-life nitrate and ammonium sensors in the form of a monitoring system for abandoned polluted areas or landfills.

One important advantage of the present invention is the insertion of an aqueous inner phase during the supply of material being bled out. A particularly advantageous embodiment is obtained if the aqueous inner electrolyte (which is typically used to drain the inner potential) of a polymer membrane electrode is supersaturated or saturated with the important compounds. Thus, there will be a continuous supply from the inner solution in the case of extraction of the plasticizing agent or of the electroactive compound into the measured solution. The effective concentrations are very low, and the influence of such an inner solution on the electrochemical behavior is correspondingly weak as well. This is not true when these compounds are brought into direct contact with the polymer membrane. Consequently, the insertion of the aqueous inner electrolyte solution is significant according to the present invention. A type of supersaturation in relation to the uptake capacity of the inner polymer membrane surface occurs when the compounds in question (the plasticizing agent in question and the electroactive compound) are supplied to the inner solution via an inner carrier with a substantially larger surface. Chromatographic carrier with the same membrane cocktail as that used to prepare the electrode, coated and fixed in a perforated capsule in the inner solution, is used in a preferred embodiment. To achieve even higher supersaturations of the inner solution with the extractable (bleedable) membrane components, the actual polymeric carrier (PVC, polycarbonate, polyacrylamide, polysiloxanes, etc.) may be eliminated during the coating on the chromatographic carrier material (e.g., Chromosorb, firebricks, silica gel, aluminum oxide, etc.). The corresponding plasticizing agent and the corresponding electroactive compound (corresponding to the membrane composition of the polymer measuring electrode) are coated on this chromatographic carrier material of especially large surface at the same ratio as in the polymer measuring electrode, even though other ratios are also suitable, as was demonstrated by comprehensive measurement series. The ratio of the surface of the ion-selective polymer membrane to the surface of the larger surface carrier is substantially lower than one, and typically even less than 0.001, with such larger surface carrier, for instance, being in the form of a perforated conditioning cartridge located immediately adjacent each corresponding side of the ion-selective polymer membrane.

Another advantage of the present invention is that the enrichment of more lipophilic interfering ions in the membrane phase during the contact time with the sample solution is prevented from occurring in order for effect b) mentioned above not to take place. This is achieved by the measured ion being introduced into the ion solution at a relatively high concentration. As a result, it usually occurs there associated with the electroactive compound (e.g., bound to an ionophore or as an ion pair with the ion-exchange compound) and it is able to penetrate as such into the polymer membrane and thus to replace the components extracted into the measured solution from the inner side of the polymer membrane. Since the supply of measured ions is substantially higher as a result than the supply of interfering ions from the measured solution, the dominant measured ion-exchange current density is continuously maintained as a consequence. Flow injection analysis must be performed at higher interfering ion concentrations, which are ruled out in the groundwater monitoring process proposed, because it makes it possible to keep the contact time of the measured solution with more lipophilic interfering ions so short that the thermodynamic distribution equilibrium cannot become established. In addition, contrary to the general procedure in FIA, an appreciable measured ion concentration is added to the carrier electrolyte here. As a result, the dominant measured ion exchange current density can be maintained for the longest time possible, together with the molecules of the electroactive compound diffusing from the inside of the membrane, which compound also transports measured ions into the membrane.

Using these devices according to the present invention, it has been possible to reach usage times exceeding one year so far in the case of typical nitrate- and ammonium-selective PVC membrane electrodes (of the size of a cigarette).

The novel ISEs of this drastically prolonged usage time (not to be confused with life or storage time, during which interfering extraction processes can be prevented), are used in a process according to the present invention for monitoring breakthroughs into the groundwater in landfills or abandoned polluted areas. What is novel in this process is that contact of the landfill or of the polluted soil with the groundwater is indicated by a systematic and opposite change in the nitrate and ammonium concentrations in the groundwater flow in front of and behind the contact zone, rather than by the appearance of any conductive elements or compounds. The reduction in the nitrate concentration and the increase in the ammonium concentration are based on the conversion of nitrate nitrogen into ammonium nitrogen by the microbiological activity in these polluted zones. A simple leaching of soil layers by rainwater does not show an increase either in both the nitrate and ammonium concentrations or in the nitrate concentration alone. The presence of a hazard potential is indicated only by an increase in the ammonium concentration along with a simultaneous decrease in the nitrate concentration compared with the values measured before flow through the polluted area, because the groundwater body is in direct contact with the polluted zone. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings.

1: Immediately after preparation; detection limit $2 \times 10^{-6}$ moles/L, slope 55.1 mV/KD 2: After an operating time of one year; detection limit $1.4 \times 10^{-6}$ moles/L, slope 54.8 mV/KD.

DETAILED DESCRIPTION OF THE PREFERRED EMBODIMENT

Effective and correct temperature compensation is of crucial significance for a nitrate and ammonium sensor that can really be used for a long time, especially under non-thermostatted conditions. The principle of the present invention is based on the idea of replacing the hitherto usual potential drain systems of the ion-selective electrodes, which are based on an electrode of a second type (usually Ag/AgCl), with an exclusive redox system with inert metal electrodes (e.g., platinum, gold, etc.); only specific redox systems with exactly defined boundary conditions are used according to the present invention.

Figure 1A:
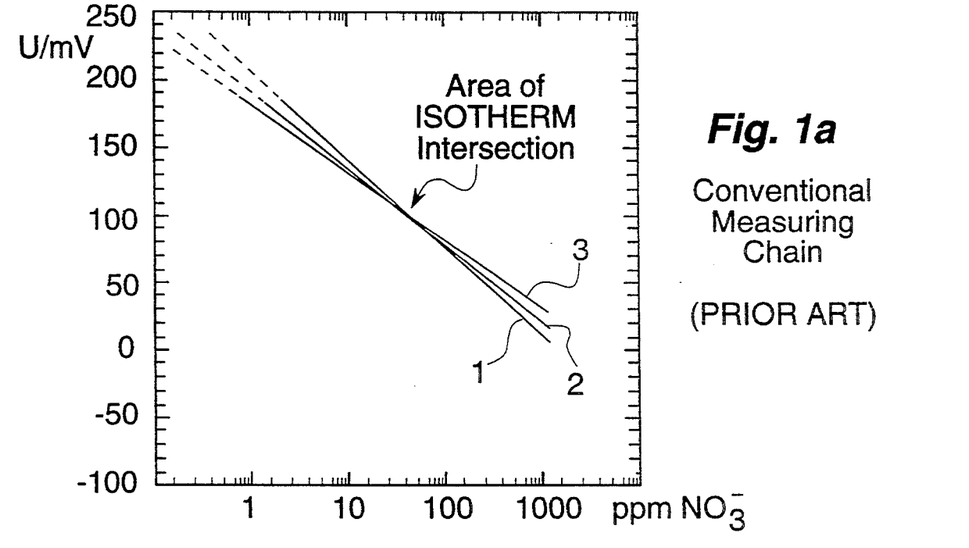
FIG. 1a shows a conventional measuring chain.

The first condition that must be met to accomplish the task according to the present invention (here; low temperature dependence) is the use of a stable redox system (which does not change chemically, besides the change in the state of the charge) with the highest possible standard exchange current density (or, in other words, with the highest possible reversibility). The second essential condition is that the so-called isotherm intersection of the potentiometric measuring chain be placed such that a) it will be approximately in the middle of the concentration range to be measured and b) it is located at ca. 0 mV. This is illustrated in FIG. 1.

Figure 1B:
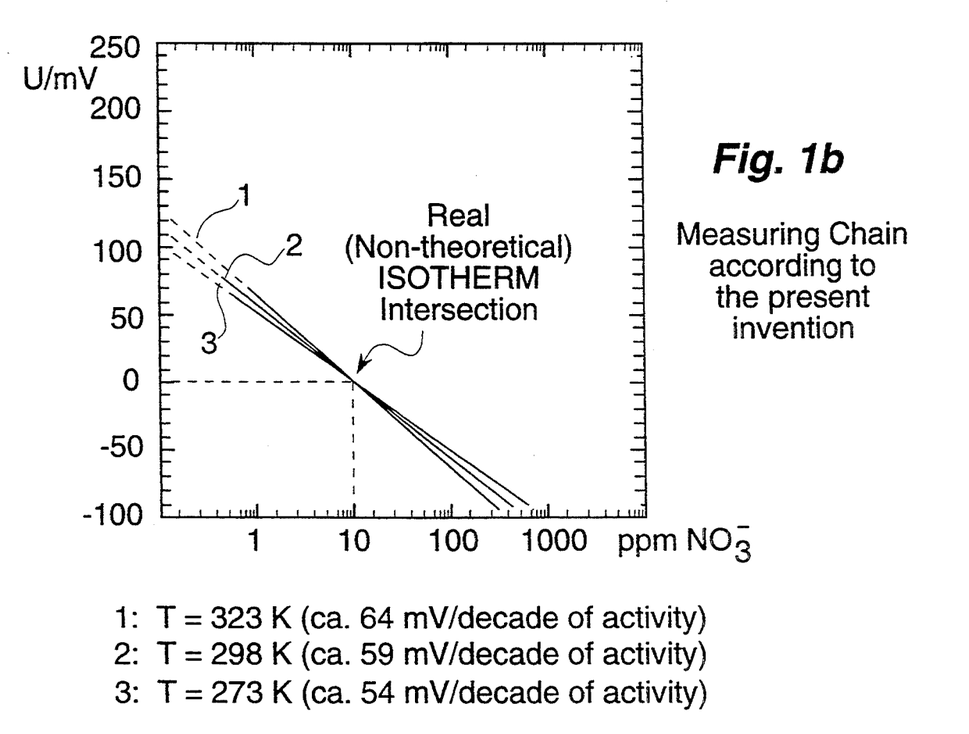
FIG. 1b shows the measuring chain according to the present invention.

This displacement of the isotherm intersection according to FIG. 1b is achieved according to the present invention by empirically varying the ratio of the concentration of the oxidized form to that of the reduced form of the redox system in terms of a corresponding potential shift, based on the subsequent conditions of use (depth of immersion, effect of the thermodiffusion potential, etc.). The concentration of the measured ions in the inner solution of the ISE and the ratio of the oxidized form to the reduced form of the redox system that is used in the outer reference electrode are used as additional variation parameters to achieve the effect according to the present invention, i.e., a conventional reference electrode is replaced according to the present invention with a novel electrode. The redox systems used within the ISE do not have to be identical to those which are used in the outer reference electrode. The latter is preferably also formed by a wire (surface) of an inert precious metal (platinum, gold, etc.), and in the concentration range from the saturated solution to $10^{-4}$ moles/L, the reversible redox system is separated from the sample solution by an additional salt bridge (=double salt bridge reference electrode), which is filled with a KCl solution. Corresponding to the clever selection of redox systems with known standard electrode potential Uo, the latter potential can be shifted by 59.16 mV/z (z=number of exchanged electrons) at 25° C. for any change in the [Ox]/[Red] ratio by a factor of 10. Greater displacements can be achieved by the combination of various redox systems with different Uo values.

The significance of the present invention will be emphasized in the following examples, which symptomatically show the drastic advantageous improvements in the properties.

Example 1: Nitrate ISE with a Device for Prolonging the Usage Time

A particularly advantageous nitrate sensor based on a polymer membrane measuring electrode can be obtained with the following membrane composition:

50-80 wt. % plasticizing agent (e.g., dibutyl sebacate, dibutyl phthalate), 20-50 wt. % PVC and 1-5 wt. % electroactive compound (e.g., quaternary ammonium salt).

Figure 2:
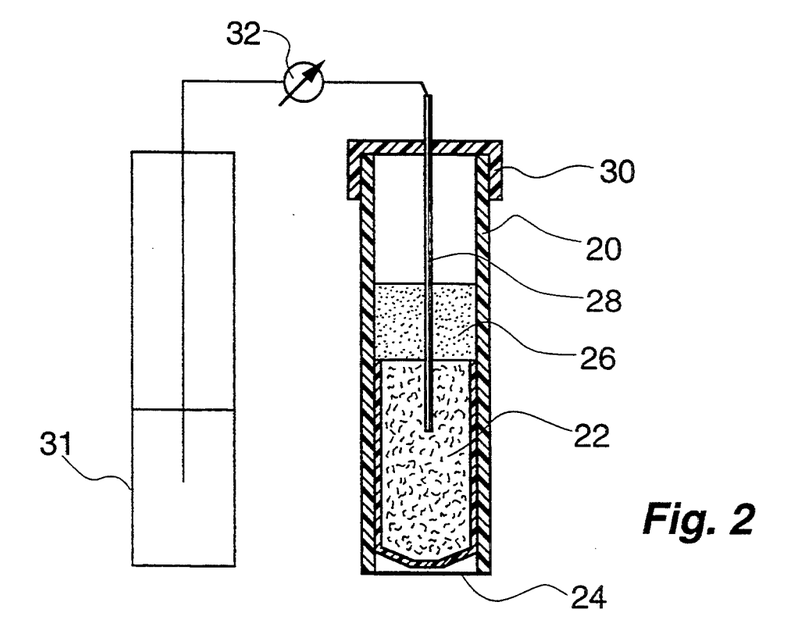
FIG. 2 shows a sketch of the nitrate sensor with self-regenerating PVC membrane.

The ion-selective polymer membrane is prepared in thicknesses of 30-200 μm according to the usual specifications K. Cammann, "Das Arbeiten mit ionenselektiven Elektroden" 1. Auflage, Springer Verlag, Berlin, 1973. The finished membrane is then glued to a PVC electrode body 20, on the inside of which four grooves with a depth of ca. 0.5 mm, which are arranged uniformly within the PVC tube, are located over the entire length. An enriching column from the firm of J. T. Baker is used here as a reservoir 22 for the mixture of plasticizing agent and electroactive compound. The packing material consists of a phenyl-substituted, modified silica gel of a particle size of 40 μm. Because of its large specific surface, this material is able to adsorb a considerable amount of plasticizing agent and electroactive compound dissolved in it. However, it is also possible to use other materials with large specific surfaces. Before this enriching column is charged, a mixture of 1.5 g tetradodecylammonium bromide, dissolved in 25 mL dibutyl phthalate, is first prepared, and this mixture is subsequently shaken several times with 0.1-mole/L $NaNO_3$. This procedure is used to recondition the modified tetradodecylammonium bromide into the nitrate form. The organic phase is suctioned through the Baker column by means of a syringe. The outer jacket is then sawed off to a length of ca. 25 mm, so that the syringe-shaped projection is obtained. This cartridge-like insert exactly fits the PVC electrode body 20 with an internal diameter of 11 min. It is carefully pushed, with the sawed-off tip in front, from the top into the polymer membrane electrode in the downward direction until it has a distance of ca. 1 mm from the PVC membrane 24 (cf. FIG. 2). The electrode modified with this device is then filled with the inner solution. The inner solution 26 contains $0.1 \times 10^{-3}$ moles/L nitrate solution as well as a suitable amount of chloride in order to achieve a stable potential for the Ag/AgCl drain 28 and to shift at the same time the working point of the entire measuring chain into isotherm intersection (without using a redox system drainage). A closing cap 30 closes the device at the top. The drain 28 electrically connects the electrode body 20 and its components via a millivoltmeter (sensor) 32 with an outer reference electrode 31 (cf. FIG. 2) so as to provide a flow measurement cell system. The sample solution being measured is placed into flow contact with the outer side of the PVC membrane 24 remote from the inner side thereof which faces the reservoir 22 defining an inner conditioning cartridge (containing the modified silica gel packing material) within the hollow interior of the electrode body 20.

This nitrate polymer membrane measuring electrode with the device according to the present invention for prolonging the usage time has a slope of 58.4 mV±10 rel. % for the linear range of the calibration curve. In contrast to all conventional polymer membrane ISEs, the slope remained constant during the entire usage time (>1 year!). The selectivity behaved similarly as well. The selectivity coefficient, which is most important for groundwater measurements, is that with respect to chloride ions. It also remained constant throughout at 0.01! The detection limit in the ppb range also remained constant during the entire period. These excellent improvements, which actually made it possible to use this ISE in a groundwater monitoring system, were measured in flow measurement with real groundwater samples (at flow rates in the range of L/hour). The end of the usage time of the device according to the present invention was not reached due to the bleeding out of important membrane components as usual, but due to calcification or biofouling (algae) of the membrane surface, which occurred only after >1 year and must be prevented by other measures. An occasional removal by decalcifying agents (e.g., EDTA) or biocides is helpful here.

Example 2: Cross Interference-Free Ammonium ISE with a Process for Prolonging the Usage time The selectivity of the prior-art $NH_4^+$ ISE with respect to other monovalent cations is usually insufficient for the interference-free determination of ammonium in drinking-water and groundwater samples. It is therefore advantageous to separate the ammonium ions in this case. This can be done in situ and on-line by alkalization (pH >10), because all the ammonium occurs as $NH_3$ gas under these conditions. This can be collected through a membrane that is permeable to gas (e.g., one made of hydrophobic materials, such as teflon, silicone rubber, etc.) in a neutral receiving liquid (e.g., 0.01 mole/L Tris-HCl buffer, pH=7.00), in which it again occurs 100% as $NH_4^+$ ions. Since no other interfering ions are able to pass through the hydrophobic membrane, the ammonium ion is present in this solution without interfering ions, and it is now possible to use the typical $NH_4^+$-selective ISE based on Nonactin K. Cammann, "Das Arbeiten mit ionenselektiven Elektroden" 1. Auglage, Springer Verlag, Berlin, 1973. Since the sample does not come into direct contact with the measuring electrode itself in this procedure, but a second auxiliary electrode is used as the receiver for the gaseous $NH_3$, this solution can be conveniently saturated or supersaturated with the plasticizing agent or the corresponding electroactive compound. It is advantageous to add the compounds that usually tend to bleed out immediately at the time of preparation of this buffer solution while heating. Further additives are added to avoid biofouling (e.g., addition of azide) or to set a constant reference electrode potential in an advantageous measuring chain without conversion. When the receiving solution flows continuously past the measuring electrode in the $\mu L$/minute range, quasi-continuous and absolutely interference-free ammonium measurements in groundwater and drinking-water samples are possible by means of an FIA-like unit.

Figure 3:
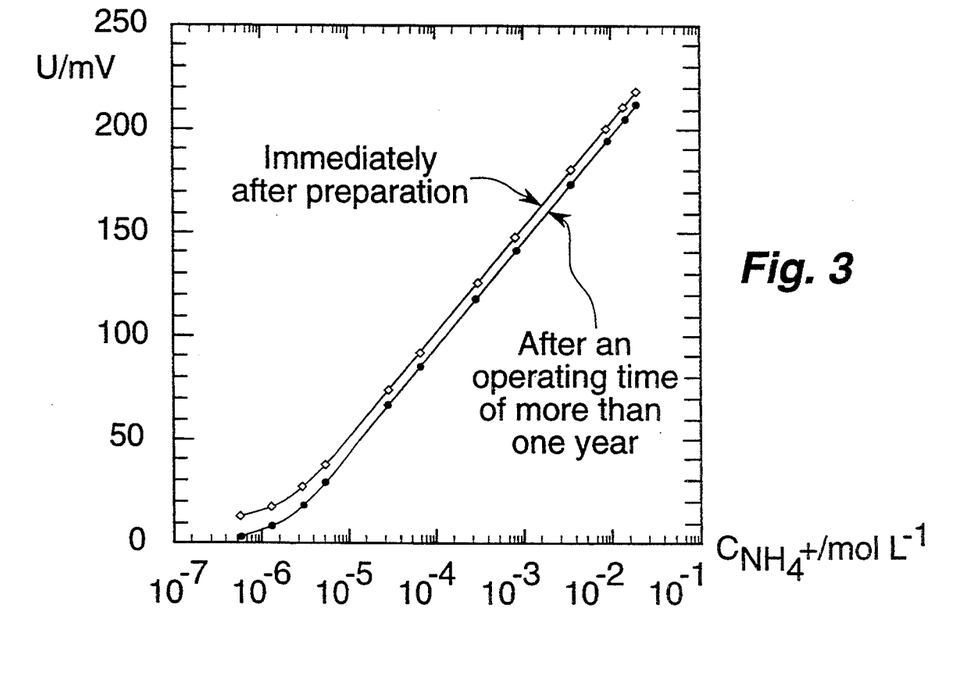
FIG. 3 shows calibration curves of the $NH_4^+$ sensor in 0.01 moles/L Tris-HCl (pH 7.0)

FIG. 3 shows two calibration curves of the above-described $NH_4^+$ sensor, which were recorded at an interval of more than one year of continuous contact with the auxiliary solution (under flow conditions). The slope has changed only insignificantly from an initial value of 55.1 mV/decade to 54.8 mV/decade! The detection limit even improved from $2 \times 10^{-6}$ to $1.4 \times 10^{-6}$ moles/L (ppb range!). The advantage over usual processes in flow measurements in ISE, in which the usage time is only a few months, is clearly obvious.

Similar prolongations of the action time can also be observed, in general, when the sample solution is passed through a conditioning column (as was mentioned in Example 1), which contains the corresponding compounds for in situ saturation, prior to contact with the measuring electrode membrane in ISE measurements without separation step (as in the example above).

Example 3: Arrangement for the Long-Term Measurement of Ammonium and Nitrate in Groundwater (Monitoring Measuring Probe)

Figure 4:
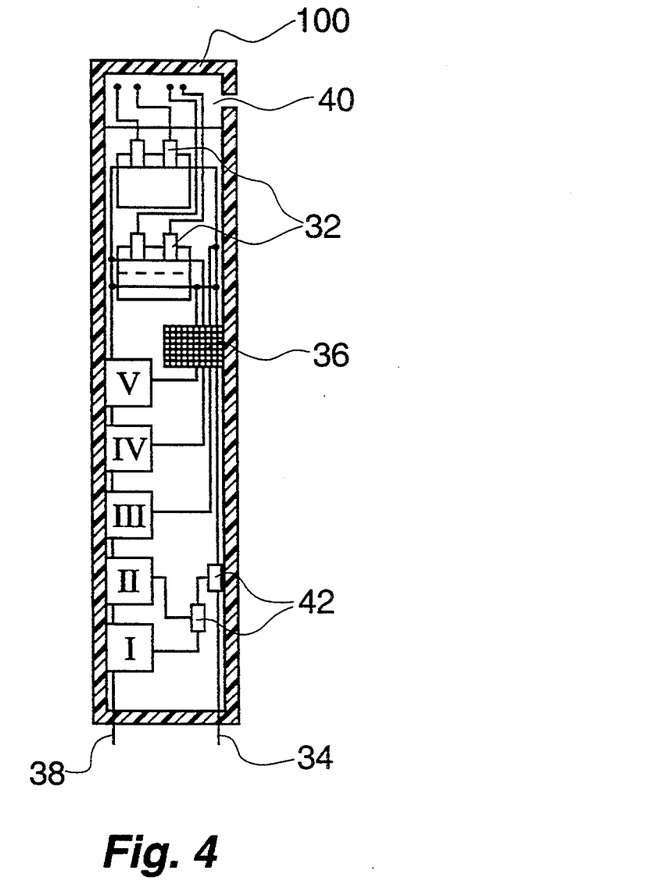
FIG. 4 shows the schematic design of a groundwater monitoring system.

Polymer membrane ISEs of the above-described design are combined in this example into a complete, automatically operating measuring system for advantageous use of the longer-life measuring electrodes. FIG. 4 schematically shows the design of a monitoring measuring probe for the continuous or quasi-continuous determination of ammonium and nitrate in groundwater and drinking-water samples. The measuring probe is located in a sealed housing 100 and fits into the typical 4-inch boreholes used for groundwater probing. The reserve of calibrating and conditioning solutions is sufficient for operation for about one year in groundwater. For monitoring landfill or abandoned polluted areas, at least one measuring probe must be installed in the upstream area (before passage through the hazard area), and at least one measuring probe must be installed in the downstream area. If desired, another pair of such measuring probes may be positioned for comparison at a similar distance from one another in the groundwater outside a hazard area. Solutions are provided in solution reservoirs I-V. These solutions include a calibrating solution 1, calibrant solution 2, auxiliary reagent solution 1, auxiliary reagent solution 2 and auxiliary reagent solution 3. The reservoirs I-V are connected to sensors 32 via conduits and are likewise connected to an intake 34. The intake, the reservoirs I-V and the sensors are all connected via pump 36. A discharge 38 is also connected to the reservoirs. The intake 34 is connected to a first two-way valve 42 which in turn is connected to a second two-way valve 42 (connecting reservoirs I and II. The sensors 32 are connected to electronic connections such as a monitoring unit 40.

The device may be used for monitoring of groundwater with opposite changes in the concentrations of nitrate and ammonium wherein the electronic outputs may be evaluated with electronic data processing and intermediate data storage in a RAM pack at the site of the measurement wherein data poling may be performed as needed to a central unit by telemetry.

The groundwater sample is suctioned from intake 34 by means of a central peristaltic pump 36 via a filter in the mL/minute range. The filter may consist of a conditioning column (charged with plasticizing agent and electroactive compound). For the nitrate measurement, the sample is also mixed with a 0.01-mole/L NaF solution (III) for setting a constant ionic strength, before it flows past a nitrate-measuring electrode designed according to Example 1 in a flow-measuring cell (sensor 32). A fluoride electrode can also be used as a reference electrode in a corresponding position here, because the fluoride content in the auxiliary electrolyte remains constant. As a result, the need to refill salt bridge electrolyte in conventional reference electrodes is eliminated. The two calibrating solutions I and II consist of $NH_4NO_3$ solutions, which enclose the desired measuring range of the probe for ammonium and nitrate ions. These calibrating solutions are protected with biocides against algal growth. They are sent through the FIA-like unit for calibration instead of the sample solution only when needed. Part of the sample flow is branched off for the determination of ammonium, and it is mixed with 0.1-mole/L NaOH (IV) before this partial flow is passed through the gas diffusion cell. The alkaline solution flows through an especially flat channel in front of a gas-permeable membrane here. The so-called acceptor solution for the $NH_3$ gas passing through (V: 0.15 moles/L Tris-HCl, pH 7.0) flows in a similarly flat channel on the other side of this membrane. This solution is transported more slowly than the sample solution in order to achieve high sensitivity in the ppb range. An $NH_4^+$-selective polymer membrane electrode, which was mentioned in Example 2, but which additionally also contains an inner conditioning cartridge for prolonging the usage time, is used as the ammonium sensor. In addition, solution V is saturated or supersaturated with the corresponding plasticizing agent and with the corresponding electroactive compound. A chloridized silver wire is used as the reference electrode, because no other interfering ions can reach this side of the gas-permeable membrane.

To save chemicals, the liquid flows are possibly transported with miniaturized feed pumps (36) of constant capacity. Since the ion-selective measuring chain can be operated in flow cells with small dead volume, pump capacities in the $\mu L$/minute range are completely sufficient. The ion concentrations now occurring can be conveniently collected by an ion-exchange column at the outlet of the probe in order to prevent pollutants from entering the groundwater. To ensure an especially economical use of the five solutions in the measuring probe, the measurement may also be performed intermittently rather than continuously. To do so, the measuring electrodes are advantageously stored in a conditioned calibrating solution (saturated with plasticizing agent and electroactive compound) in the waiting position. The polymer membrane becomes positive due to the constant supply of measuring ions, i.e., it is conditioned for measuring ions in the interest of a high standard exchange current density.

The actual measurement is conducted automatically in this procedure, either at predetermined time intervals or as needed, when changes occur in the concentrations in the sample. These changes can be indicated by the ISE measuring chain at reduced accuracy and reliability immediately behind the sample intake filter. A measuring chain, in which an ammonium ISE, is connected against a nitrate ISE is advantageous here, i.e., a reference electrode with salt bridge electrolytes to be refilled is not used here, either. The above-mentioned combination of two measuring electrodes indicates a constant measuring chain voltage at constant $NH_4^+$ and $NO_3^-$ values. If the ammonium content in the measured solution increases when the ammonium ISE is connected to the measuring electrode input, and the nitrate ISE is connected to the reference electrode input of the measuring instrument, the measuring chain voltage increases at constant nitrate content. The measuring chain voltage decreases in this circuit in the case of increasing nitrate contents and constant ammonium contents. Since it is very unlikely for opposite changes in the concentrations of the two ions to exactly compensate the Nernst relationship, this measuring chain signal can be used to control the accurate measurement that takes place subsequently. The frequency of measurements can be adjusted to the rate of the change in order to obtain more accurate recordings of sudden changes in the concentrations of the two ions.

Example 4: Minimizing the Temperature Coefficient of ISE Measuring Chains

ISE measuring chains for long-term measurements are better designed without the usual reference electrodes with a KCl salt bridge, because this requires an additional solution in the measuring probe, and because the temperature dependence of so-called saturated calomel or silver/silver chloride reference electrodes is too complicated and too slow. Supersaturation phenomena have been known to lead to hysteresis phenomena and consequently to a behavior that cannot be compensated. Redox electrodes with especially reversible redox systems with a high standard exchange current density (e.g., hexacyanoferrates II+III; iodine/iodide, ferrocene/ferrocenium, ruthenium complexes, etc.), display a better behavior in this respect. Since the sample solution is diluted with conditioning solution in the measuring probe arrangement anyway, it is logical to add a redox system at a suitable concentration to this conditioning solution, and to use a simple platinum wire as the reference electrode. It is particularly advantageous now, because of the symmetrical design, if the inner potential drainage of the ISE is based on the same system, in which case a cationic redox system is to be selected for anion-selective ISEs and an anionic redox system for cation-selective ISEs.

To minimize the temperature dependence of such ISE measuring chains with platinum redox reference electrode, the so-called isotherm intersection of the measuring chain must be determined under the subsequent measuring conditions. This intersection of the calibration curves at the different temperatures is now shifted into the range around zero by cleverly changing the inner solution of the ISE and of the redox system in the measuring solution. The variables are now a) the measured ion concentration in the ISE and b) the ratio of the oxidized form to the reduced form of the corresponding redox system in both the inner solution of the ISE and the outer measuring solution. Should the reversible redox system be too expensive, low concentrations are also sufficient if the redox buffer capacity is assumed in this case by a less expensive system at higher concentration. This also applies to toxicological concerns.

Using the hexacyanoferrate II/III system, it was possible to reduce the temperature dependence of the complete measuring system for ammonium and nitrate to an error of <0.1% per degree of deviation between calibration and measurement between 1° C. and 15° C.

While specific embodiments of the invention have been shown and described in detail to illustrate the application of the principles of the invention, it will be understood that the invention may be embodied otherwise without departing from such principles.

I claim:

1. Device for prolonging the effective usage time and for minimizing temperature effects in an ion-selective polymer membrane electrode measuring chain, comprising an ion-selective polymer membrane electrode having an ion-selective membrane defining an outer side and an inner side, which membrane contains a plasticizing agent and an electroactive compound which tend to bleed out therefrom, an outer aqueous measured solution immediately adjacent the outer side of the membrane and an inner aqueous potential drain solution immediately adjacent the inner side of the membrane, conditioning means for supplying the plasticizing agent and electroactive compound to the outer solution and inner solution for saturating such solutions therewith, and a redox drain element arranged for shifting an isotherm intersection of an ion-selective measuring chain into a middle of a measuring range, said middle being approximately 0 mV.

2. Device of claim 1 wherein the conditioning means include a perforated outer conditioning cartridge for supplying the plasticizing agent and electroactive compound to the outer solution and a perforated inner conditioning cartridge for supplying the plasticizing agent and electroactive compound to the inner solution, each cartridge containing the plasticizing agent and electroactive compound adsorbed on a corresponding highly disperse solid phase of large specific surface.

3. Device of claim 2 wherein a ratio of a surface of the membrane to a surface in each cartridge is substantially lower than one.

4. Device of claim 3 wherein the ratio is less than 0.01.

5. Device of claim 2 wherein the solid phase of large specific surface comprises finely powdered chromatographic carrier material of particle diameter in the $\mu m$ range, and the plasticizing agent and electroactive compound are chromatographically applied to the surface thereof.

6. Device of claim 2 wherein each cartridge contains a selectivity-generating electroconductive compound together with a measured ion as an ionophore complex or ion pair compound.

7. Device of claim 2 wherein the polymer electrode defines a hollow interior communicating with the exterior thereof through the membrane such that the inner side of the membrane faces the hollow interior and the outer side of the membrane faces the exterior of the polymer electrode, the inner conditioning cartridge is located in the hollow interior, and the outer conditioning cartridge is located exterior to the polymer electrode such that the measured solution flows therethrough for filtering the measured solution prior to contact thereof with the outside of the membrane.

8. Device of claim 1 wherein the conditioning means are arranged for supplying the plasticizing agent and electroactive compound to the outer solution and inner solution such that the plasticizing agent and electroactive compound are prevented from coming into direct contact with the membrane and thus from impairing the electrochemical properties thereof.

9. Device of claim 1 wherein the polymer electrode is connected electrically with a constant potential reference electrode via a millivoltmeter to form a complete potentiometric measuring cell defining a measuring chain, the redox drain element is provided in a potential determining reversible redox system, with high standard exchange current density on a precious metal, with or without an additional redox buffer, for correspondingly defining an inner drain system and an outer drain system for the membrane, and the inner solution contains measured ions at a concentration which places an isotherm intersection of the complete potentiometric measuring cell at approximately 0 mV and into said middle of the measuring range in order to minimize temperature effects on measurement results.

10. Device of claim 9 wherein precious metal redox electrodes are provided for performing an inner and outer potential drain from the membrane.

11. Device of claim 9 wherein redox systems are provided for the inner potential drain within the polymer electrode and for the reference electrode such that a redox system which is provided for the inner potential drain within the polymer electrode is not identical to a redox system which is provided for the reference electrode.

12. Device of claim 9 wherein a reversible redox system is provided wherein temperature dependence of the $U°$ term in an associated Nernst equation is compensated.

13. Device of claim 9 wherein additional redox systems with corresponding redox buffer capacity, which impose a redox potential to a reversible system, are provided besides the potential determining reversible redox system.

14. Process for prolonging the effective usage time and for minimizing temperature effects in an ion-selective polymer membrane electrode measuring chain, comprising providing an ion-selective polymer membrane electrode having an ion-selective membrane defining an outer side and an inner side, which membrane contains a plasticizing agent and an electroactive compound which tend to bleed out therefrom, electrically connected with a constant potential reference electrode via a millivoltmeter to form a complete potentiometric measuring cell defining a measuring chain, providing an outer aqueous measured solution immediately adjacent the outer side of the membrane and an inner aqueous potential drain solution immediately adjacent the inner side of the membrane, supplying the plasticizing agent and electroactive compound to the outer solution and inner solution for saturating such solutions therewith, and shifting an isotherm intersection of an ion selective measuring chain into a middle of a measuring range, said middle corresponding approximately to 0 mV, with a redox drain element.

15. Process of claim 14 wherein the measuring chain is employed for nitrate and ammonium groundwater monitoring by removing ammonium ions in gaseous ammonia form from groundwater as measured solution by alkalization, collecting the gaseous ammonia by means of a gas diffusion cell in an auxiliary solution for measurement with an ammonium ion-selective electrode.

16. Process of claim 15 wherein an automatic measurement of nitrate and ammonium ions in the groundwater as measured solution is effected by means of a flow injection analyzer sample preparation with an ionic strength adjuster and redox buffer, upon development of a change in the concentration the nitrate and ammonium ions in the sample preparation flow.

17. Process of claim 16 wherein changes in the concentration of the nitrate and ammonium ions in the groundwater as measured solution are determined by a measuring electrode combination of an ammonium ion-selective polymer membrane electrode connected against a nitrate ion-selective polymer membrane electrode and positioned directly in the sample preparation flow after the point of supplying the plasticizing agent and electroactive compound thereto.

18. Process of claim 17 wherein upon a preselected change in the measuring chain voltage per unit time of the $NH_4^+/NO_3^-$ ion-selective polymer membrane electrode combination, the groundwater as measured solution is continuously conducted thereto for continuous determination of ammonium and nitrate ions in the sample preparation flow.

19. Process of claim 17 wherein the ammonium and nitrate polymer membrane electrodes are maintained during intervals between measurements in an ammonium nitrate conditioning solution containing the plasticizing agent and electroactive compound.

20. Process of claim 19 wherein the conditioning solution is in the form of a calibrating solution containing the highest ammonium and nitrate contents corresponding to the measuring range of the measuring chain and also containing the plasticizing agent and electroactive compound.

21. Process of claim 17 wherein the measuring electrode combination of an ammonium ion-selective polymer membrane electrode and nitrate ion-selective polymer membrane electrode is replaced by a plurality of identical polymer membrane electrodes and which are introduced into the sample preparation flow by remote control for increasing the usage time of the measuring chain.

* * * * *